United States Patent
Ikawa et al.

[11] Patent Number: 6,142,664
[45] Date of Patent: Nov. 7, 2000

[54] MOLTEN METAL PROBE

[75] Inventors: Osamu Ikawa; Yasunori Iwamoto, both of Nishihonmachi, Japan

[73] Assignee: Kawaso Electric Industrial Kabushiki Kaisha, Osaka, Japan

[21] Appl. No.: 09/222,913

[22] Filed: Dec. 30, 1998

[30] Foreign Application Priority Data

Jan. 20, 1998  [JP]  Japan .................................. 10-023738

[51] Int. Cl.⁷ .............................. G01K 1/12; G01N 1/12
[52] U.S. Cl. ........................................ 374/140; 73/864.55
[58] Field of Search ......................... 73/864.59, 864.55, 73/DIG. 9, 864.56, 864.57; 374/140

[56] References Cited

U.S. PATENT DOCUMENTS

| | | | |
|---|---|---|---|
| 3,646,816 | 3/1972 | Hance et al. ........................ | 73/DIG. 9 |
| 4,002,069 | 1/1977 | Takemura et al. ..................... | 374/140 |
| 4,048,857 | 9/1977 | Bardenheuer et al. ................ | 374/140 |
| 4,102,197 | 7/1978 | Bardenheuer et al. ................ | 374/140 |
| 4,401,389 | 8/1983 | Theuwis ............................... | 73/864.55 |
| 4,699,014 | 10/1987 | Boron ................................... | 73/864.55 |
| 4,896,549 | 1/1990 | Falk ...................................... | 374/140 |
| 5,515,739 | 5/1996 | Baerts ................................... | 73/864.55 |

FOREIGN PATENT DOCUMENTS

3039027 10/1982 Germany .............................. 374/140

*Primary Examiner*—Diego Gutierrez
*Assistant Examiner*—Stanley J. Pruchnic, Jr.
*Attorney, Agent, or Firm*—Nixon Peabody LLP; David S. Safran

[57] ABSTRACT

A molten metal probe which is dipped into molten metal and thereafter pulled up therefrom and which is capable of preferably providing solidification temperature data of the molten metal and providing a solidified sample. A probe main body includes an introductory path facing a flow inlet formed at a side portion thereof, a communicating path and a sampling path branched respectively upwardly and downwardly from the introductory path, a temperature measuring chamber communicated with the communicating path extended upwardly, a sampling chamber communicated with the sampling path extended downwardly, and a temperature sensor facing the temperature measuring chamber.

13 Claims, 9 Drawing Sheets

MOLTEN METAL PROBE

BACKGROUND OF THE INVENTION

1. Field of the Invention

The present invention relates to a molten metal probe used mainly for sampling and analyzing a sample of molten metal such as molten steel.

2. Description of Related Art

As is publicly known conventionally, a molten metal probe is dipped into molten steel of a converter or the like by an elevating apparatus referred to as a sub-lance, pulled up therefrom and utilized for carrying out analysis of content or the like of molten steel.

A probe main body is provided with a flow inlet for flowing in molten steel at a side portion thereof, the inside of the probe main body is installed with a deoxidizing chamber for passing therethrough the flowed-in molten steel and a sampling chamber which also serves as a temperature measuring chamber (hereinafter called as the sampling/temperature-measuring chamber) for solidifying the deoxidized molten steel in a stored state, and a temperature sensor is arranged in the sampling/temperature-measuring chamber.

Normally, the deoxidizing chamber and the sampling/temperature-measuring chamber are formed by a vessel which can be regarded as a single piece as a whole. The vessel is constituted by bringing a pair of small vessels opposedly in abutment with each other and interposing a partition plate therebetween, the deoxidizing chamber is provided by the upper small vessel with the partition plate as a boundary and the sampling/temperature-measuring chamber is provided by the lower small vessel. Further, a through hole is formed in the partition plate and the temperature sensor which is inserted into the deoxidizing chamber from a top wall of the upper small vessel, is inserted into the sampling/temperature-measuring chamber via the through hole. Further, an introductory hole communicating with the flow inlet of the probe main body is opened at a side portion of the upper small vessel providing the deoxidizing chamber.

Hence, molten steel which flows in via the introductory hole, firstly passes through the deoxidizing chamber, passes through the through hole of the partition plate and advances into and is stored in the sampling/temperature-measuring chamber. Molten steel which fills the sampling/temperature-measuring chamber and successively flows therein is stored in the deoxidizing chamber.

The sampling/temperature-measuring chamber is surrounded by a wall made of a metal, solidifies swiftly molten steel stored there and provides a small lump of solidified molten steel as a sample for instrumental analysis such as emission spectra analysis or combustion chemical analysis.

Molten steel stored in the sampling/temperature-measuring chamber gradually solidifies from the surrounding and a temperature measuring unit of the temperature sensor is made to face a portion where the molten steel finally solidifies by which solidification temperature data for determining carbon content of the molten steel is provided.

According to the constitution of the conventional technology, the pair of small vessels are brought into abutment with each other via the partition plate and are integrated and held at inside of the probe main body to constitute a vessel the total of which is regarded as a single piece and therefore, the assembling operation is not facilitated.

The probe main body needs a paper pipe having a large diameter for constituting an outer cylinder and a paper pipe having a small diameter for constituting an inner cylinder and the inner cylinder is fitted into the outer cylinder in a state in which the vessel is integrated at inside of the inner cylinder.

When the probe main body is dipped into molten steel, the molten steel which flows thereinto via the introductory hole, firstly passes through the deoxidizing chamber, passes through the through hole of the partition plate, is stored in the sampling/temperature-measuring chamber and fills this chamber, and subsequently further molten steel which successively flows thereinto is stored in the deoxidizing chamber.

As is publicly known, the molten steel includes a large amount of oxygen and therefore, the deoxidizing chamber is previously charged with a deoxidizer such as an Aluminum piece. Therefore, the flowed-in molten steel is deoxidized in passing through the deoxidizing chamber and stored and solidified in the sampling/temperature-measuring chamber in a deoxidized state. However, the molten steel which has flowed in from the flow inlet, flows only through a single path reaching the sampling/temperature-measuring chamber via the deoxidizing chamber and therefore, when the deoxidizer is melted and exhausted by the initially flowed-in molten steel, molten steel which successively flows thereinto is no longer deoxidized. Therefore, the successive undeoxidized molten steel flows into the sampling/temperature-measuring chamber and is mixed with molten steel which has formally advanced thereinto and stored there, as a result, there poses a problem in which blow holes owing to nondeoxidization is caused in the solidified sample.

Meanwhile, the probe main body which has been pulled up from molten steel is dropped from a high location toward a floor face. Then, the vessel which has sampled the sample is taken out from the probe main body, the solidified sample is taken out from the vessel and the sample is carried by carrying means such as a pneumatic tube for instrumental analysis. However, in the case of the conventional technology in which the deoxidizing chamber and the sampling/temperature-measuring chamber are constituted by the vessel which is regarded as a single piece as a whole, the sample which has solidified in the sampling/temperature-measuring chamber and unnecessary solidified metal which has solidified in the deoxidizing chamber are connected to each other to thereby form one small lump and therefore, it is difficult to disassemble the pair of small vessels constituting the vessel and the partition plate and it is difficult to take out the solidified sample from the vessel. Further, even when the solidified sample is succeeded to take out from the vessel fortunately, before carrying the solidified sample which is an object of analysis, unless the large unnecessary solidified metal connected to the solidified sample is separated by a cutter or the like, the sample cannot be carried by the pneumatic tube.

SUMMARY OF THE INVENTION

It is an object of the invention to provide a molten metal probe resolving the above-described problem.

According to an aspect of the invention, there is provided a molten metal probe which is dipped in molten metal and is thereafter pulled up therefrom comprising a probe main body, a flow inlet provided at a side portion of said probe main body for flowing in the molten metal, a temperature measuring chamber and a sampling chamber separately provided in said probe main body for solidifying the molten metal flowed therein respectively, and a temperature sensor arranged in said temperature measuring chamber; wherein, runners branching upwardly and downwardly from an introductory path opened to face the flow inlet are provided, a sampling path constituted by the downward runner is communicated with the sampling chamber and a communicating path constituted by the runner extended upwardly is communicated with an upper portion of the temperature measuring chamber.

At least, a deoxidizer having necessary amounts are charged respectively to the sampling path, the communicating path and the sampling chamber. Accordingly, the sampling chamber is filled with only molten metal which has been preferably deoxidized by a pertinent amount of the deoxidizer when it passes through a predetermined length of the sampling path and the molten metal is stored and solidified there and therefore, a sample having no occurrence of blow hole is obtained. That is, the molten metal is efficiently deoxidized in the flow-in procedure passing through the long sampling path reaching the sampling chamber. Further, the temperature measuring chamber is filled with only molten metal which has been preferably deoxidized by a pertinent amount of the deoxidizer in passing through a predetermined length of the communicating path, the molten metal is stored and solidified there and accordingly, no blow hole is caused at a finally solidified portion facing a temperature measuring portion of the temperature sensor and accurate solidification temperature data is provided.

Further, heat of the molten metal is pertinently taken out in passing through the long communicating path reaching the temperature measuring chamber and accordingly, the volume of the temperature measuring chamber can be reduced and further, emergence of a balanced portion of a waveform of solidification temperature outputted from the temperature measuring sensor is accelerated and the waveform can be measured stably.

It is possible to communicate the sampling path directed downwardly with a vicinity of a terminal end of the introductory path, communicate the communicating path directed upwardly with a vicinity of an opening of the introductory path such that the communicating path and the sampling path branched upwardly and downwardly from the introductory path in this way are arranged not to be opposed to each other but to shift from each other in respect of the branch point. Further, it is possible that a center axis line C2 of the sampling path directed downwardly and a center axis line C3 of the communicating path directed upwardly are shifted from each other and a distance L2 from a center axis line C1 of the probe main body to the center axis line C2 and a distance L3 therefrom to the center axis line C3 are brought under a relationship of L2<L3. Further, it is preferable that the communicating path directed upwardly is constituted by a linear path substantially in parallel with the center axis line of the probe main body and an inclined path extended toward a vicinity of an opening of the introductory path by being bent from the linear path. In this case, it is preferable that the introductory path is formed with a raised portion projected upwardly from a lower face of an opening portion facing the flow inlet at a vicinity of a terminal end of the introductory path and the sampling path directed downwardly is opened at a top portion of the raised portion. By such a selective constitution, when molten metal filled in the communicating path after filling the temperature measuring chamber with the molten metal, flows down from the communicating path to the introductory path in pulling up the probe main body, the molten metal is prevented from being brought into contact with the molten metal filled in the sampling path and being solidified integrally and is preferably discharged from the flow inlet to outside.

Further, according to the invention, there is provided a unit body molded in a block by a collapsible fire resistant material and the unit body is internally mounted to the probe main body. The unit body is formed with the introductory path opened in a side direction, the communicating path extended upwardly from the introductory path, the temperature measuring chamber extended downwardly by being turned bacl or being folded back from the communicating path, a holding chamber at outside of the temperature measuring chamber for holding the temperature sensor having a temperature measuring portion inserted into the temperature measuring chamber and a guide path extended downwardly from the introductory path. The sampling chamber is constituted by a sampling vessel separately from the unit body. According to the sampling vessel, a guide pipe extended from an inlet portion of a vessel main body made of a metal is inserted into the guide path and the sampling path is constituted by the guide pipe. The unit body is constituted by divided blocks which are divided in two pieces or parts along the central axis line of the probe main body. Therefore, operation of integrating the structures in a cylindrical body made of a paper pipe of the probe main body is facilitated and the assembling operation is significantly facilitated in comparison with the conventional case.

According to another aspect of the invention, there is provided a molten metal probe which is dipped in molten metal and is thereafter pulled up therefrom comprising a probe main body, a flow inlet provided at a side portion of said probe main body for flowing in the molten metal, a temperature measuring chamber and a sampling chamber separately provided in said probe main body for solidifying the molten metal flowed therein respectively, and a temperature sensor arranged in said temperature measuring chamber; further comprising: a plug internally mounted to a front end portion of the probe main body and a unit body internally mounted to the probe main body in a state in which the unit body is connected to the plug; wherein, the plug and the unit body are separately formed and are molded in blocks respectively by a collapsible fire resistant material; the unit body includes an introductory path opened to face the flow inlet, a communicating path extended upwardly from the introductory path, the temperature measuring chamber extended downwardly by being turned back from the communicating path, a guide path extended downwardly from the introductory path and a free space formed by expanding a lower portion of the guide path and opened to a lower face of the unit body; the plug includes a holding recess opposed to the free space; and a sampling vessel constituting the sampling chamber provides a vessel main body made of metal with a guide pipe extended therefrom and inserted into the guide path, an upper portion of the vessel main body is loosely inserted to the free space and a lower portion of the vessel main body is fitted to the holding recess.

According to another aspect of the invention, there is provided a molten metal probe which is dipped in molten metal and is thereafter pulled up therefrom comprising a probe main body, a flow inlet provided at a side portion of said probe main body for flowing in the molten metal, and a sampling chamber provided in said probe main body for receiving and storing the flowed-in molten metal; further comprising: a plug internally mounted to a front end portion of the probe main body and a unit body internally mounted to the probe main body in a state in which the unit body is connected to the plug; wherein, the plug and the unit body are formed separately and molded in blocks respectively by a collapsible fire resistant material; the unit body includes an introductory path opened to face the flow inlet, a guide path extended downwardly from the introductory path and a free space formed by expanding a lower portion of the guide path and opened to a lower face of the unit body; the plug includes a holding recess opposed to the free space; and a sampling vessel constituting the sampling chamber provides a vessel main body made of metal with a guide pipe extended therefrom and inserted into the guide path, an upper portion of the vessel main body is loosely inserted into the free space and a lower portion of the vessel main body is fitted to the holding recess.

According to the constitution of the invention, when the probe main body pulled from the molten metal is dropped from a high location to a floor face, the unit body and the plug are collapsed by impact of drop and accordingly, the sampling vessel sampled with the solidified sample can easily be taken out. According to the invention, in the vessel main body of the sampling vessel, the lower portion is fitted to the holding recess of the plug and the upper portion is inserted smoothly into the free space of the unit body. Therefore, until achieving the object of sampling the molten metal, the sampling vessel is held by the holding recess and in the meantime, in the state of being dipped into the molten metal, the plug is gradually made fragile and is partially collapsed and accordingly, after sampling the molten metal, the exposed sampling vessel can easily be taken out from the free space of the unit body.

According to another aspect of the invention, there is provided a molten metal probe which is dipped in molten metal and is thereafter pulled up therefrom comprising a probe main body, a flow inlet provided at a side portion of said probe main body for flowing in the molten metal, a temperature measuring chamber and a sampling chamber separately provided in said probe main body for solidifying the molten metal flowed therein respectively, and a temperature sensor arranged in said temperature measuring chamber; further comprising: an extended unit body internally mounted to a front end portion of the probe main body and molded in a block by a collapsible fire resistant material to form integrally a plug shell portion facing a front end of the probe main body and a unit shell portion extended therefrom; wherein, the unit shell portion includes an introductory path opened to face the flow inlet, a communicating path extended upwardly from the introductory path, the temperature measuring chamber extended downwardly by being turned back from the communicating path and a guide path extended downwardly from the introductory path; the plug shell portion includes a containing chamber communicating with the guide path and a receiving chamber arranged in parallel with the containing chamber in a laterally arranged state and opened downwardly; a sampling vessel constituting the sampling chamber provides a vessel main body made of metal with a guide pipe extended therefrom and inserted into the guide path, the vessel main body is fitted to the containing chamber; and outside temperature measuring means is inserted into and held by the receiving chamber.

Preferably, the unit shell portion is provided with the holding chamber at outside of the temperature measuring chamber for holding a holder portion of the temperature sensor, the temperature sensing portion of the temperature sensor is inserted into the temperature measuring chamber, and a wire connecting space portion is formed to open at a side portion of the extended unit body and communicates with a hole opened at a bottom wall of the receiving chamber of the plug shell.

Further preferably, the extended unit body comprises divided blocks which are divided in two pieces or parts along the center axis line of the probe main body.

BRIEF DESCRIPTION OF THE DRAWINGS

FIGS. 2A, 2B, 2C, 2D and 2E show cross sections of a probe main body adopted in the embodiment of the invention in which

DETAILED DESCRIPTION OF THE PREFERRED EMBODIMENTS

A detailed description will be given of preferred embodiments of the invention in reference to drawings as follows.
(First Embodiment)

As shown by FIG. 1 through FIG. 4, a probe main body 1 is integrated with a necessary structure at inside of a cylindrical body 2 made of a paper pipe. A flow inlet 3 for flowing in molten metal such as molten steel or the like is opened at a side portion of the cylindrical body 2 and the flow inlet 3 is closed by an outer skin 4 made of a comparatively thin paper pipe covering outer periphery of the cylindrical body 2. According to the probe main body 1, an extension pipe 5 made of a paper pipe extending upwardly is connected to an elevating apparatus of a sublance and the probe main body 1 is dipped into molten metal such as molten steel in a converter and is pulled up thereafter. In dipping thereof, the outer skin 4 burns off when it reaches molten metal bath after passing through a slag layer to thereby make the flow inlet 3 open and makes the molten metal flow into the probe main body 1.

The cylindrical body 2 of the probe main body 1 is internally mounted with a plug 6 and a unit body 7 which are molded in blocks by a collapsible fire resistant material, respectively. As the fire resistant material, for example, inorganic particles of foundry sand can be used. According to a molded article molded by a primary process for stamping a group of particles, the group of particles are bound via a resin binder by a secondary process of a sintering process at high temperatures or a chemical adhering process by using gases at normal temperature. Further, a film formed by a mold coating agent can be provided on the surface of the unit body 7 including an introductory path 8, a communicating path 9 and a temperature measuring chamber 10 as necessary. The molded article formed in this way is made fragile and becomes gradually more collapsible from the surface by burning off the resin binder when it is dipped into molten metal. As illustrated, in respect of the unit body 7 inserted into a vicinity of a front end of the cylindrical body 2, the plug 6 is insertingly attached to an opening at the front end of the cylindrical body 2 by which the plug 6 and the unit body 7 are bonded in series.

The unit body 7 is formed with the introductory path 8 which is opened to face the flow inlet 3 of the cylindrical body 2, the communicating path 9 extending upwardly from the introductory path 8 and the temperature measuring chamber 10 extending downwardly by being folded back from the communicating path 9 and the introductory path 8 and the temperature measuring chamber 10 are arranged to distribute substantially in left and in right in respect with a central axis line of the unit body 7. Further, a guide path 11 extended downwardly from the introductory path 8 is formed, a holding path 12 which is extended from the guide path 11 and the inner diameter of which is expanded and a free space 13 which is extended from the holding path 12 and the inner diameter of which is further expanded, are formed and the free space 13 is made to open at a lower face of the unit body 7.

Figure 4:
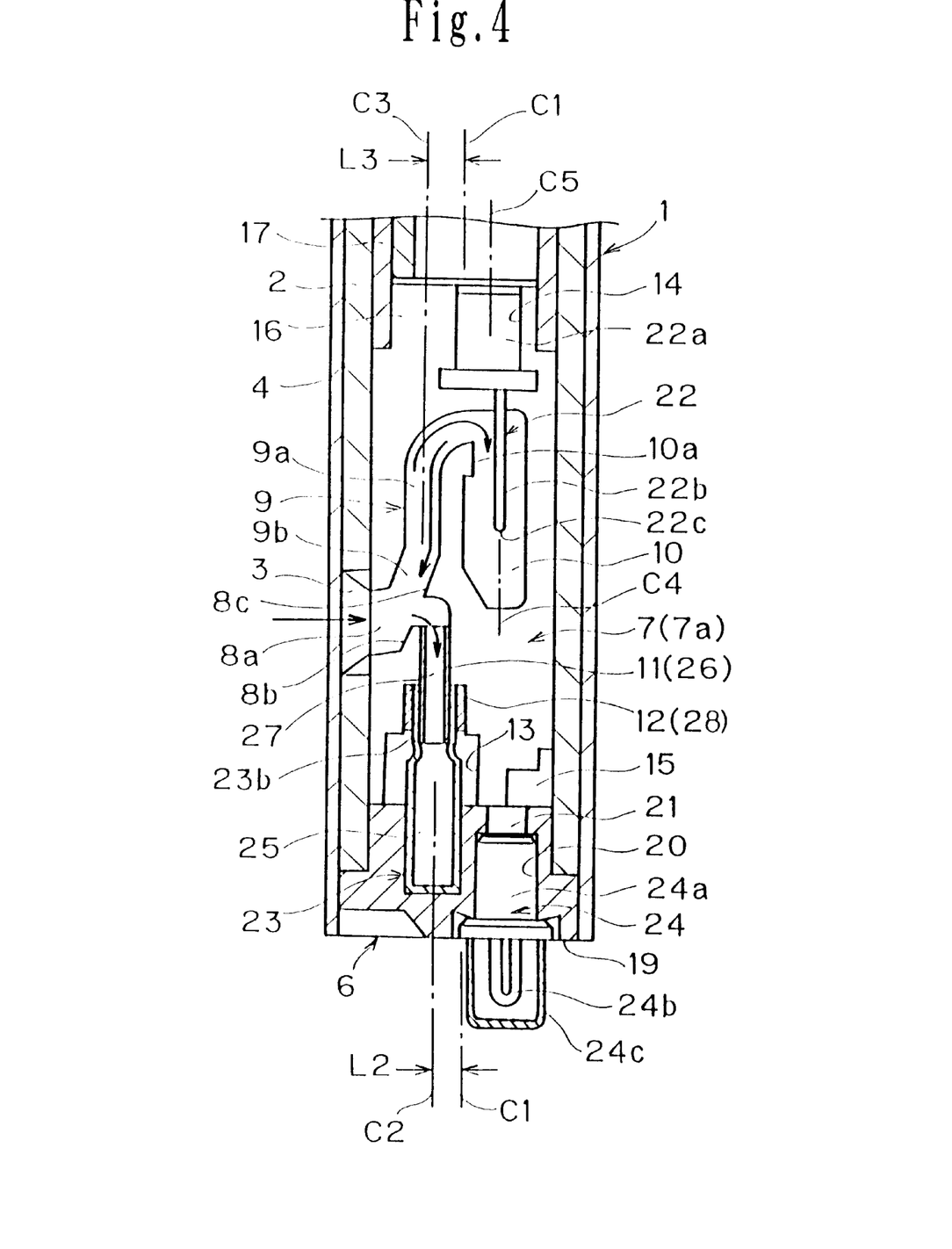
FIG. 4 is an enlarged longitudinal sectional view showing the probe main body adopted in the embodiment of the invention.

The communicating path 9 and the guide path 11 which are branched from the introductory path 8 upwardly and downwardly, are not exactly opposed to each other in respect of the branch point but is arranged to shift from each other. As illustrated, according to the introductory path 8, while a lower face of an opening portion 8a facing the flow inlet 3 is formed low, a vicinity of a terminal end of the introductory path 8 is formed high by which a raised portion 8b is formed. Further, while the guide path 11 is opened at the top portion of the raised portion 8b, the communicating path 9 is opened to the opening portion 8a. Therefore, as shown by FIG. 4, a central axis line C2 of the guide path 11 and a central axis line C3 of the communicating path 9 are shifted from each other and a distance L2 from a central axis line C1 of the unit body 7 to the central axis line C2 of the guide path 11 and a distance L3 therefrom to the central axis line C3 of the communicating path 9 are formed under a relationship of L2<L3. Further, the communicating path 9 is provided with a linear path 9a substantially in parallel with the central axis line C1 of the unit body 7 and an inclined path 9b which is inclined to bend from the linear path and extends toward the opening 8a of the introductory path 8. As a result, a cover portion 8c is formed above the guide path 11.

Further, the unit body 7 is formed with the holding chamber 14 for holding a temperature sensor mentioned later above the temperature measuring chamber 10 and is formed with a drawing groove 15 for drawing a lead wire of an outside temperature measuring means mentioned later, at a vicinity of the free space 13. Further, as shown by a chain line in FIG. 1, an extension groove 15a along a side portion of the unit body 7 may be formed to extend from the drawing groove 15.

Figure 3:
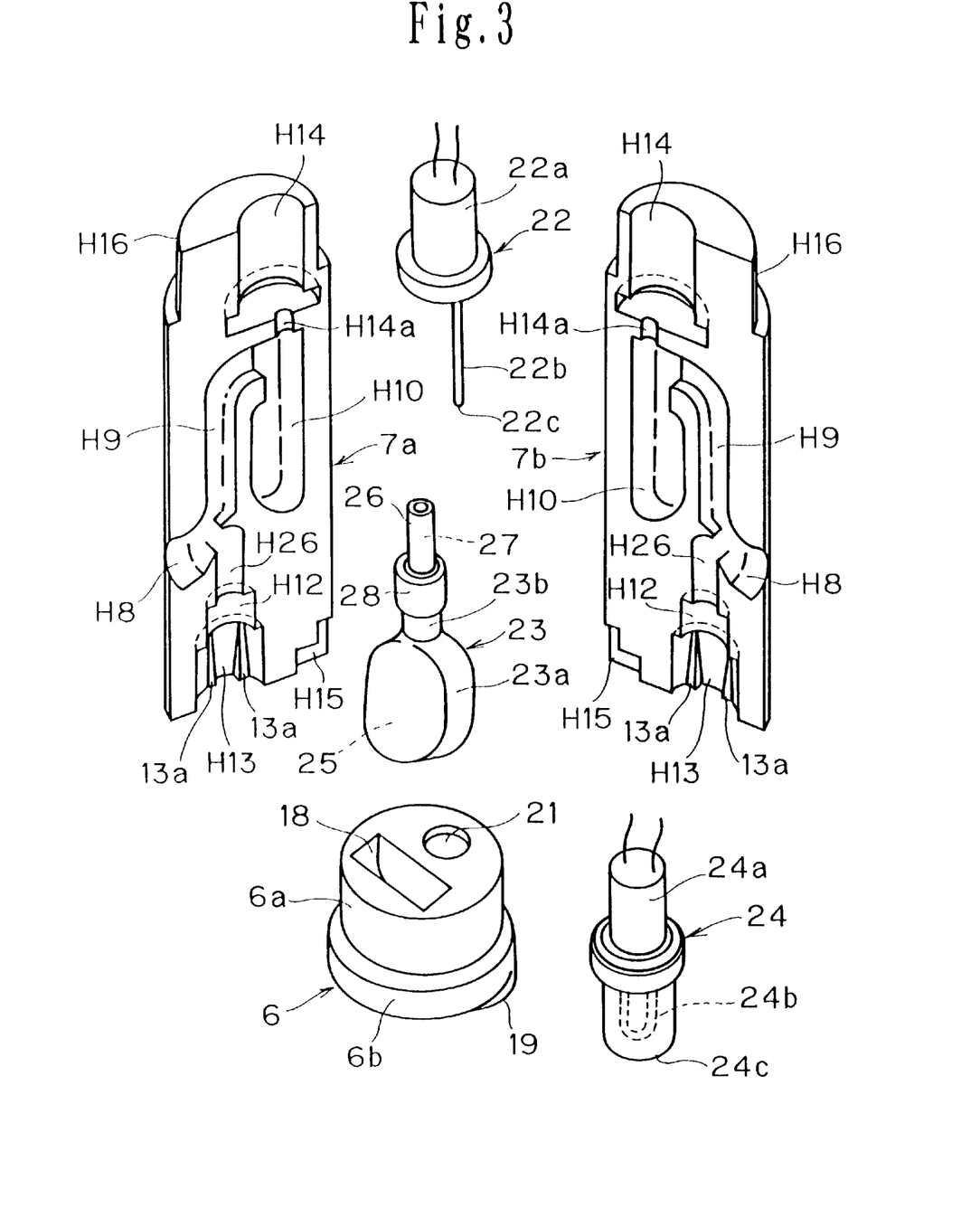
FIG. 3 is a disassembled perspective view of an inner structure of the probe main body adopted in the embodiment of the invention shown by FIG. 1.

As shown by FIG. 3, the unit body 7 is constituted by divided blocks 7a and 7b, each configuration of which is shaped by dividing the unit body 7 in two along the central axis line and integrated substantially in a circular column shape as a whole by opposing and overlapping the pair of divided blocks 7a and 7b in a symmetrical shape.

Figure 1:
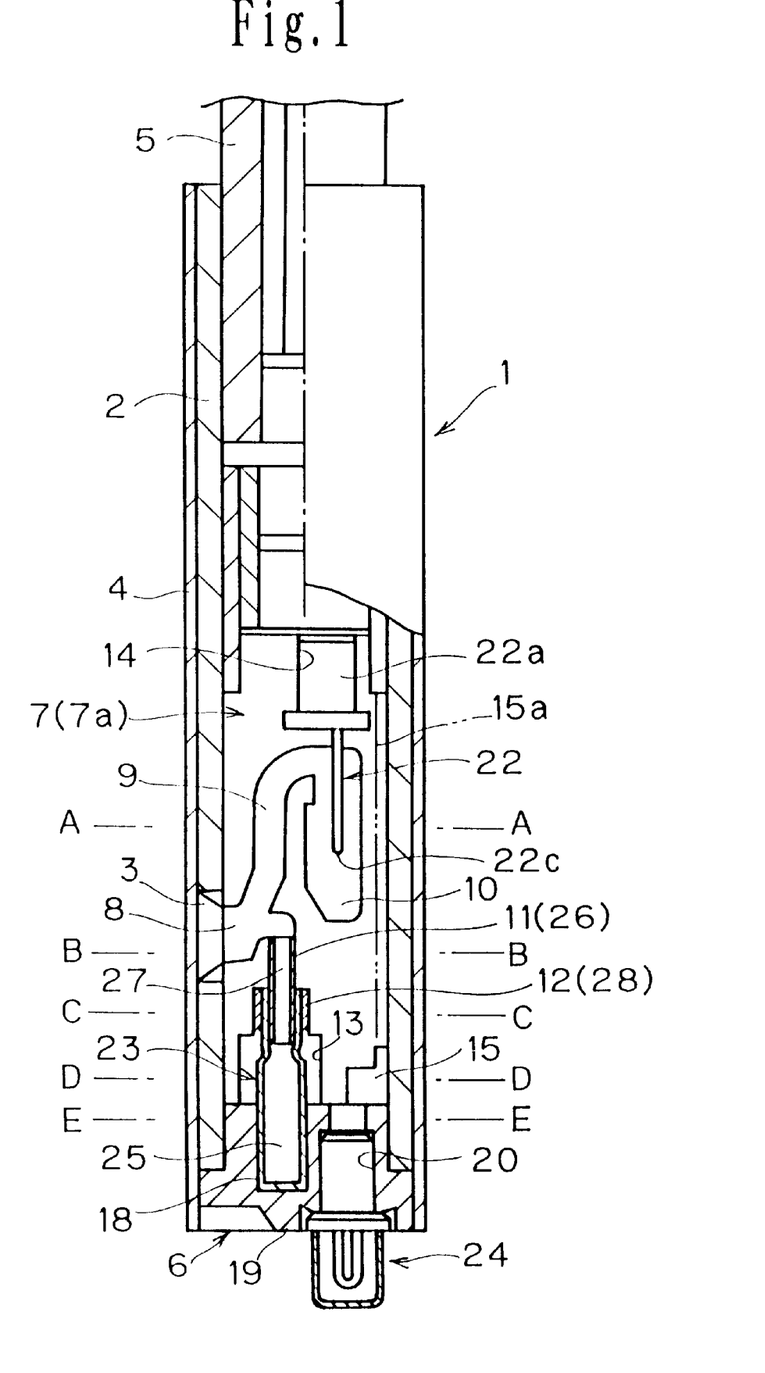
FIG. 1 is a longitudinal sectional view showing an embodiment of a molten metal probe according to the invention.
Figure 2A:
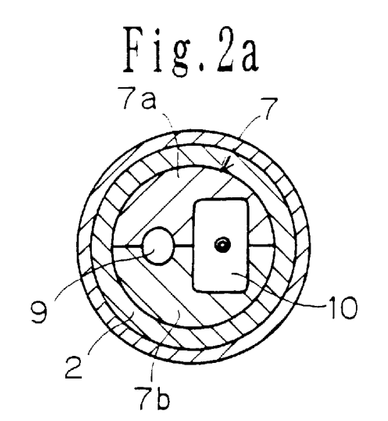
FIG. 2A is a sectional view taken from a line A—A of FIG. 1.
Figure 2B:
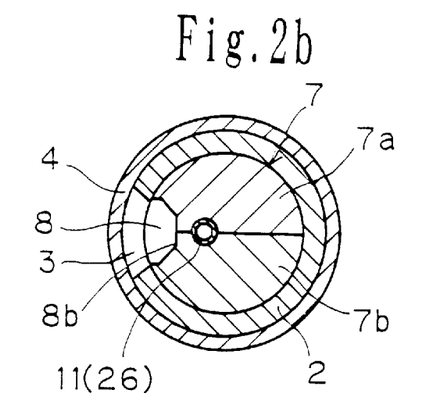
FIG. 2B is a sectional view taken from a line B—B of FIG. 1.
Figure 2C:
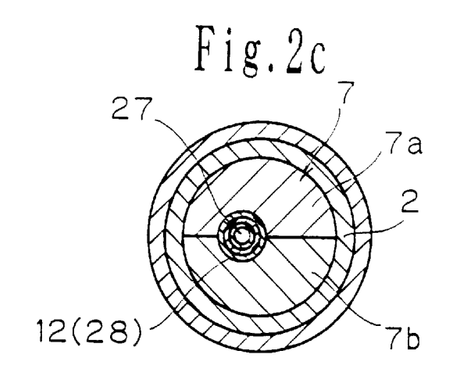
FIG. 2C is a sectional view taken from a line C—C of FIG. 1.
Figure 2D:
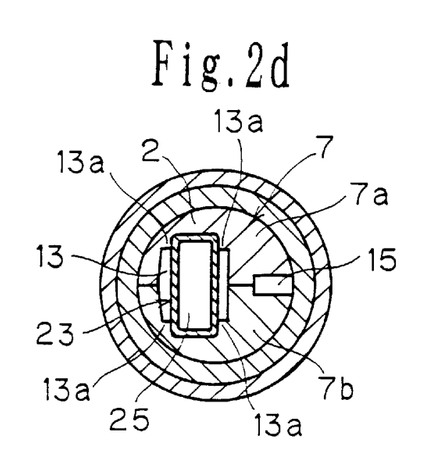
FIG. 2D is a sectional view taken from a line D—D of FIG. 1
Figure 2E:
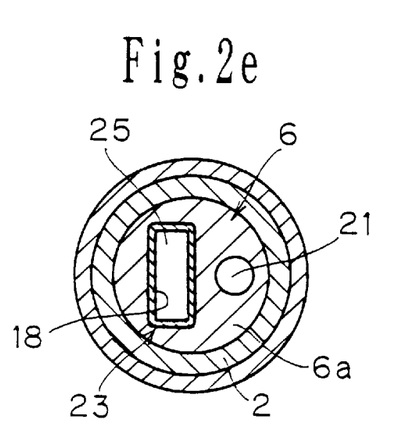
FIG. 2E is a sectional view taken from a line E—E of FIG. 1.

The upper end portion of the unit body 7 is constituted by a small diameter portion 16 having a reduced outer diameter and as shown by FIG. 1, the small diameter portion 16 is fitted to a holding cylinder 17 comprising a paper pipe in a state in which the couple of divided blocks 7a and 7b are assembled. As is apparent by viewing the disassembled state of the unit body shown by FIG. 3, at a partition wall portion disposed between the holding chamber 14 and the temperature measuring chamber 10, a through hole 14a for inserting a temperature measuring pipe of a temperature sensor 22, mentioned later, is formed. Further, at the free space portion 13, ribs 13a for positioning a sampling vessel, mentioned later, are provided. Further, as shown by FIG. 3, in the divided blocks 7a and 7b which are halved in a symmetrical shape, respective halves of the introductory path 8, the communicating path 9 and the guide path 11 which are branched from the introductory path, the temperature measuring chamber 10 and the holding chamber 14 of the unit body 7 are formed. Accordingly, in FIG. 3, constituent portions showing the halves are designated by attaching notations produced by adding H to notations designating respective structural constitutions mentioned above.

The plug 6 is provided with a circular disk portion 6a insertingly attached to a front end of the cylindrical body 2 and a flange portion 6b opposed to a front end face of the cylindrical body 2. It is preferable to interpose adhering means such as fire resistant cement between the circular disk portion 6a and the cylindrical body 2 and it is preferable that the outer periphery of the flange portion 6b is covered by the outer skin 4. The circular disk portion 6a is formed with a holding recess 18 opposed to the free space 13 of the unit body 7 further, on the lower face of the plug 6, a boss portion 19 is projected at a position deviated from the center, a holding hole 20 for holding outside temperature measuring means 24 is formed from the boss portion 19 toward the inside of the circular disk portion 6a and a drawing hole 21 for drawing lead wires is formed at the bottom portion of the holding hole 20.

The temperature sensor 22, a sampling vessel 23 and the outside temperature measuring means 24 are integrated to the plug 6 and the unit body 7 by which the probe main body 1 in the molten metal probe of the invention is formed.

The temperature sensor 22 is constituted to extend a temperature measuring pipe 22b from a holder portion 22a, a thermocouple is installed at inside of the temperature measuring pipe 22b and a temperature sensing portion 22c is provided at a front end portion of the temperature measuring pipe 22b. The temperature measuring pipe 22b is formed by, for example, a quartz pipe. In the illustrated example, as show in FIG. 4, both of the holding chamber 14 and the temperature measuring chamber 10 which are formed in a unit body 7, are formed such that a central axis line C5 of the holding chamber 14 is more proximate to the central axis line C1 of the unit body 7 than a central axis line C4 of the temperature measuring chamber 10 by which the holding chamber 14 is formed in a size sufficient for being able to hold the holder portion 22a. In correspondence therewith, according to the temperature sensor 22, the temperature measuring pipe 22b is made eccentric in respect with the holder portion 22a. Thereby, when the holder portion 22a is held by the holding chamber 14, the temperature measuring pipe 22b is inserted to a position along the central axis line C4 of the temperature measuring chamber 10 via the through hole 14a. Further, although illustration is omitted, lead wires led out from the holder portion 22a are connected to a connector installed above the unit body 7.

The sampling vessel 23 is installed with a vessel main body 23a made of metal constituting a sampling chamber 25, is provided with a guide pipe 26 extended from an inlet portion 23b of the vessel main body 23a and constitutes a sampling path 27 by the guide pipe 26. Preferably, the guide pipe 26 is constituted by a quartz pipe and is insertingly attached to the inlet portion 23b. A collar 28 is outwardly mounted on the inlet portion 23b and the color 28 is formed by, for example, a paper pipe.

In the illustrated example, the vessel main body 23a is constituted by a flat vessel in order to sample a solidified sample in a disk shape from molten metal. Hence, in mounting the sampling vessel 23 to the unit body 7, by inserting the upper portion of the vessel main body 23a into the free space portion 13 and positioning the vessel main body 23a by bringing the vessel main body 23a in line contact or point contact with the ribs 13a formed in the free space 13, the collar 28 is fitted to the holding path 12. Under the state, the guide pipe 26 is adaptably fitted to the guide path 11 and the front end of the guide pipe 26 is positioned to be flush with the top face of the raised portion 8b. The lower portion of the vessel main body 23a projected from the free space 13 is fittedly held by the holding recess 18 of the plug 6. That is, the lower surface of the vessel main body 23a is closely fitted to the holding recess portion 18 by face contact.

The outside temperature measuring means 24 is constituted to extend a temperature measuring pipe 24b comprising a quartz pipe in a U-like shape from a holder portion 24a, is provided with a thermocouple at inside of the temperature measuring pipe 24b and is installed with a cap 24c made of metal for covering the temperature measuring pipe 24b. The holder portion 24a is insertingly attached from the boss portion 19 of the plug 6 toward the holding hole 20 and the cap 24c is projected downwardly from the boss portion 19. Further, although illustration is omitted, lead wires led out from the holder portion 24a are connected through the drawing hole 21 of the plug 6 to a connector installed above the unit body 7 via the drawing groove 15 of the unit body 7.

Although illustration is omitted, a deoxidizer of an aluminum piece is charged into the communicating path 9, the sampling path 27 and the sampling chamber 25. When the probe main body 1 is moved downwardly to molten metal by an elevating apparatus of a sub-lance, the probe main body 1 is dipped into a molten metal bath by passing through a slag layer. Thereby, the cap 24c of the outside temperature measuring means 24 is melted away and temperature of molten metal is measured. Further, the outer skin 4 is burned off, the flow inlet 3 is opened and molten metal is made to flow into the inside of the probe main body 1. As shown by an arrow mark in FIG. 4, the molten metal which flowed from the flow inlet 3 into the introductory path 8 is branched upwardly and downwardly and flows toward the communicating path 9 and the sampling path 27.

Figure 5:
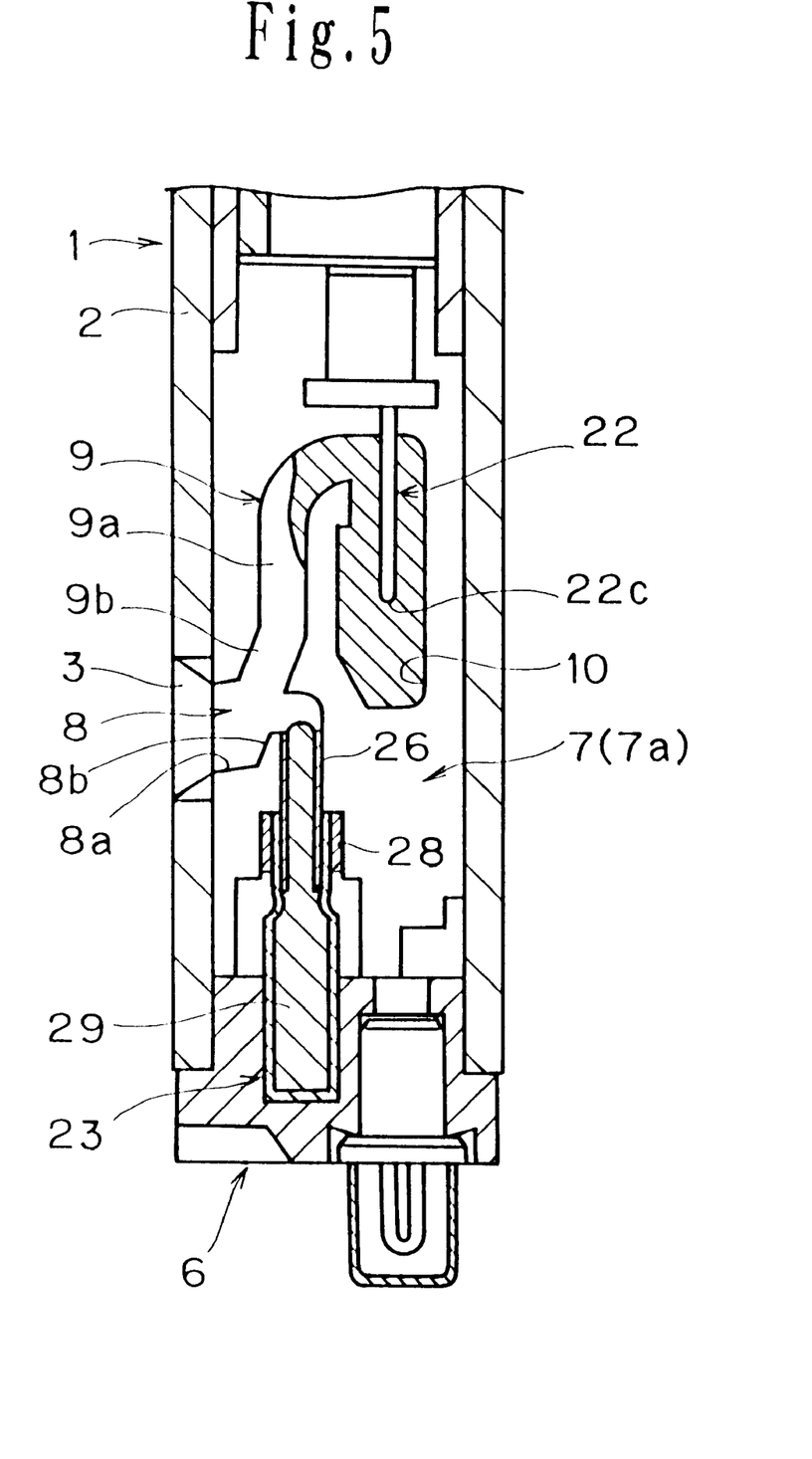
FIG. 5 is a longitudinal sectional view showing an example of a solidified state of molten metal observed when the probe main body adopted in the embodiment of the invention is dipped into the molten metal and is pulled up therefrom.

The molten metal which flows from the introductory path 8 into the long sampling path 27, is efficiently deoxidized by the deoxidizer charged to the sampling path 27 in the flow-in procedure of passing through the long sampling path 27, thereafter, flows into the sampling chamber 25, is solidified there and is provided as a solidified sample 29 for analysis such as instrumental analysis. An amount of the deoxidizer charged to the sampling path 27 is selected to a pertinent amount with no excess and deficiency in accordance with an amount of the molten metal filled in the sampling chamber 25 and accordingly, no blow hole is caused by nondeoxidation in the solidified sample 29 sampled by the sampling chamber 25 and the deoxidizer is not precipitated at inside thereof. The flowed-in molten metal is filled not only in the sampling chamber 25 but also in the sampling path 27 and the introductory path 8 and when the probe main body 1 is pulled up, molten metal discharged from the introductory path 8 toward the flow inlet 3 is separated from the molten metal filled in the sampling path 27 at a portion of the raised portion 8b. Accordingly, as shown in FIG. 5, the molten metal filled in the sampling vessel 23 provides the independent solidified sample 29 and is not provided with other unnecessary solidified metal.

The molten metal which flows from the introductory path 8 into the long communicating path 9 is efficiently deoxidized by the deoxidizer charged in the communicating path 9 in the flow-in procedure of passing through the long communicating path 9 and thereafter, flows into the temperature measuring chamber 10. At this occasion, the molten metal which flows in powerfully, advances to the communicating path 9 branched from the introductory path 8, passes through the linear path 9a via the bent inclined path 9b and reaches the temperature measuring chamber 10 by changing its direction from the linear path 9a by which the flow velocity is decelerated and heat is taken out pertinently. Accordingly, the mechanical impact and the thermal impact which the flow of the molten metal applies on the temperature measuring pipe 22b are comparatively small and accordingly, destruction of the temperature measuring pipe 22b comprising a quartz pipe is prevented. As illustrated, it is preferable to provide a projected portion 10a at a portion for communicating the communicating path 9 with the temperature measuring chamber 10 and when the inlet of the temperature measuring chamber 10 is contracted thereby, the molten metal which has flowed into the temperature measuring chamber 10 can be prevented from flowing back to the communicating path 9 by an agitating flow. The molten metal filled in the temperature measuring chamber 10 is gradually solidified from the surrounding and temperature is measured by arranging the temperature sensing portion 22c of the temperature sensor 22 substantially at the center of the temperature measuring chamber 10 and at a position having excellent thermal balance in order to obtain a balanced portion of a measured temperature value. As mentioned above, heat of the molten metal is taken out after passing through the long communicating path 9 and therefore, the volume of the temperature measuring chamber 10 can be designed to be reduced. Further, after the molten metal has filled the temperature measuring chamber 10, solidification is swiftly started. Thereby, emergence of a balanced portion in a waveform of solidification temperature outputted from the temperature measuring sensor is accelerated and a stable waveform can be measured. Further, the molten metal is deoxidized by the deoxidizer having a necessary and sufficient amount which is charged into the communicating path 9 efficiently in the flow-in procedure for passing through the long communicating path 9 and accordingly, when the molten metal is solidified in the temperature measuring chamber 10, no blow hole by deficiency in deoxidation is caused at the vicinity of the temperature measuring portion 22c and a stable and accurate solidification temperature data is provided.

Although the flowed-in molten metal is filled not only in the temperature measuring chamber 10 but also in the communicating path 9 and the introductory path 8, when the probe main body 1 is pulled up, the molten metal in the communicating path 9 is discharged from the flow inlet 3 via the introductory path 8. At this occasion, the molten metal flowing out from the communicating path 9 flows down toward the opening 8a of the introductory path 8 along the inclined path 9b. Therefore, a portion of the flowed-down molten metal is not connected to the molten metal filled in the sampling path 27. Further, as shown by FIG. 5, the molten metal filled in the temperature measuring chamber 10 is made to remain in the temperature measuring chamber 10 as unnecessary solidified metal 30 after providing solidification temperature data.

Figure 6:
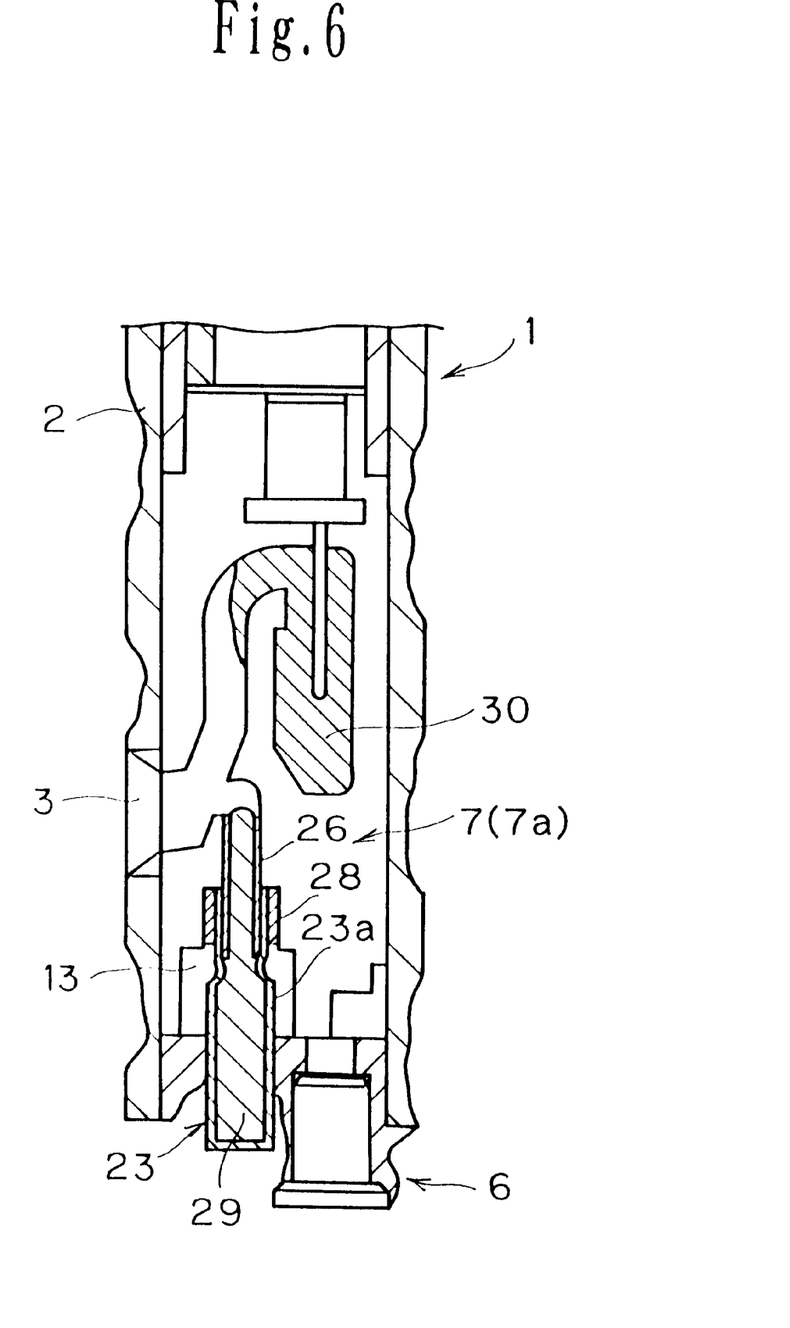
FIG. 6 is a longitudinal sectional view showing an example of a burnt state and a collapsed state when the probe main body adopted in the embodiment of the invention is pulled up from the molten metal.

According to the probe main body 1 pulled up from the bath of the molten metal, the cylindrical body 2 is considerably burnt, as mentioned above, the plug 6 is made fragile and at least the surface is collapsed and therefore, as shown by FIG. 6, the sampling vessel 23 is partially exposed. Hence, when the probe main body 1 is dropped from a high location to a floor face, the plug 6 and the unit body 7 which have been made fragile, are collapsed by impact and the sampling vessel 23 can be detached. That is, the holding recess 18 of the plug 6 has already been collapsed partially and accordingly, the sampling vessel 23 is easily detached spontaneously from the free space 13 of the unit body 7. In this case, assuming that the sampling vessel 23 cannot be detached from the unit body 7, when an operator grasps an exposed portion of the sampling vessel 23 by a jig such as a pinch, the sampling vessel 23 can easily be drawn from the free space 13. Thereafter, the sampling vessel 23 is carried by a carrying apparatus such as a pneumatic tube and is provided to analysis of instrumental analysis. Further, before the transportation, the solidified sample 29 may be taken out from the sampling vessel 23.

(Second Embodiment)

Figure 7:
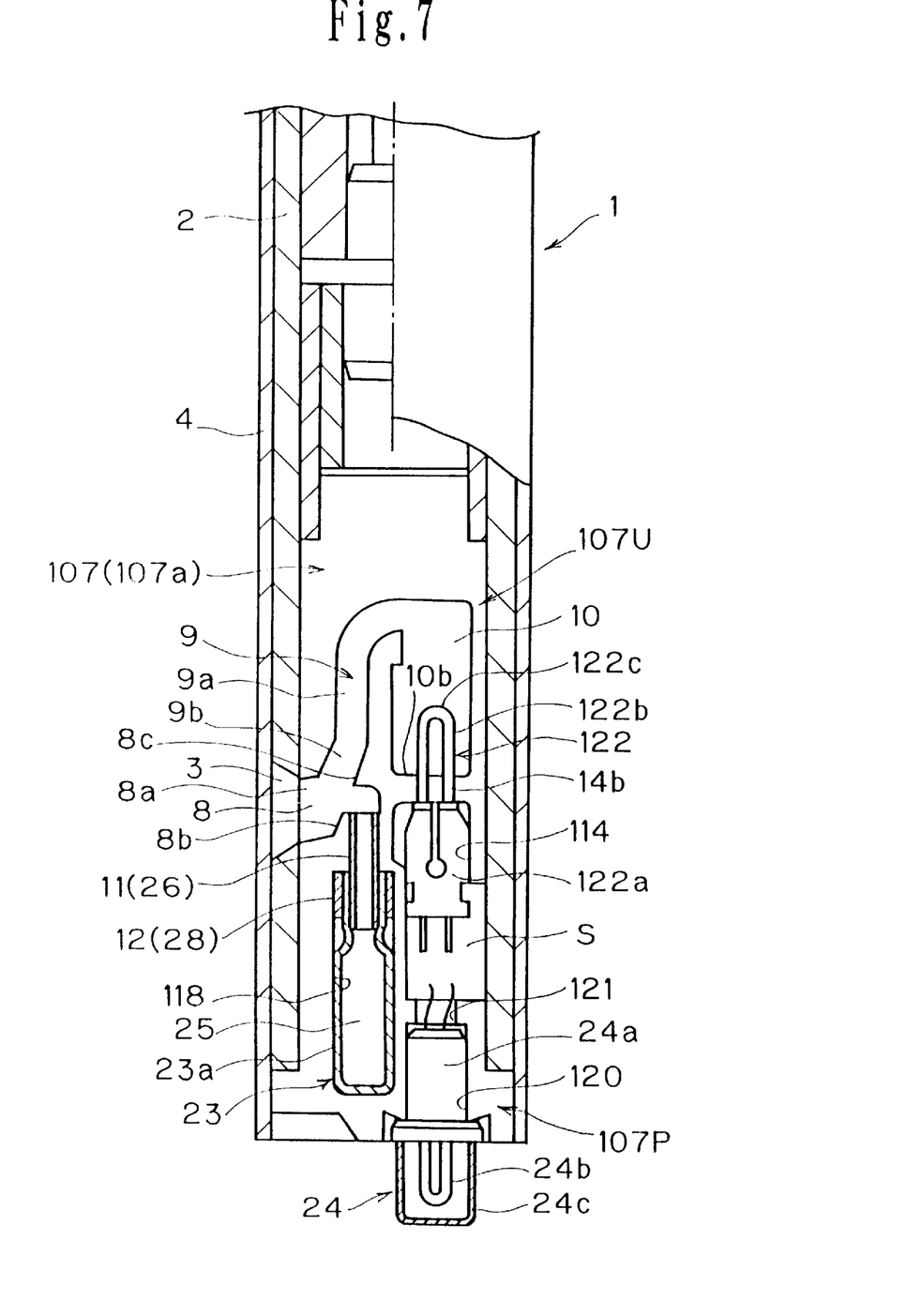
FIG. 7 is a longitudinal sectional view showing other embodiment of a molten metal probe according to the invention.
Figure 8:
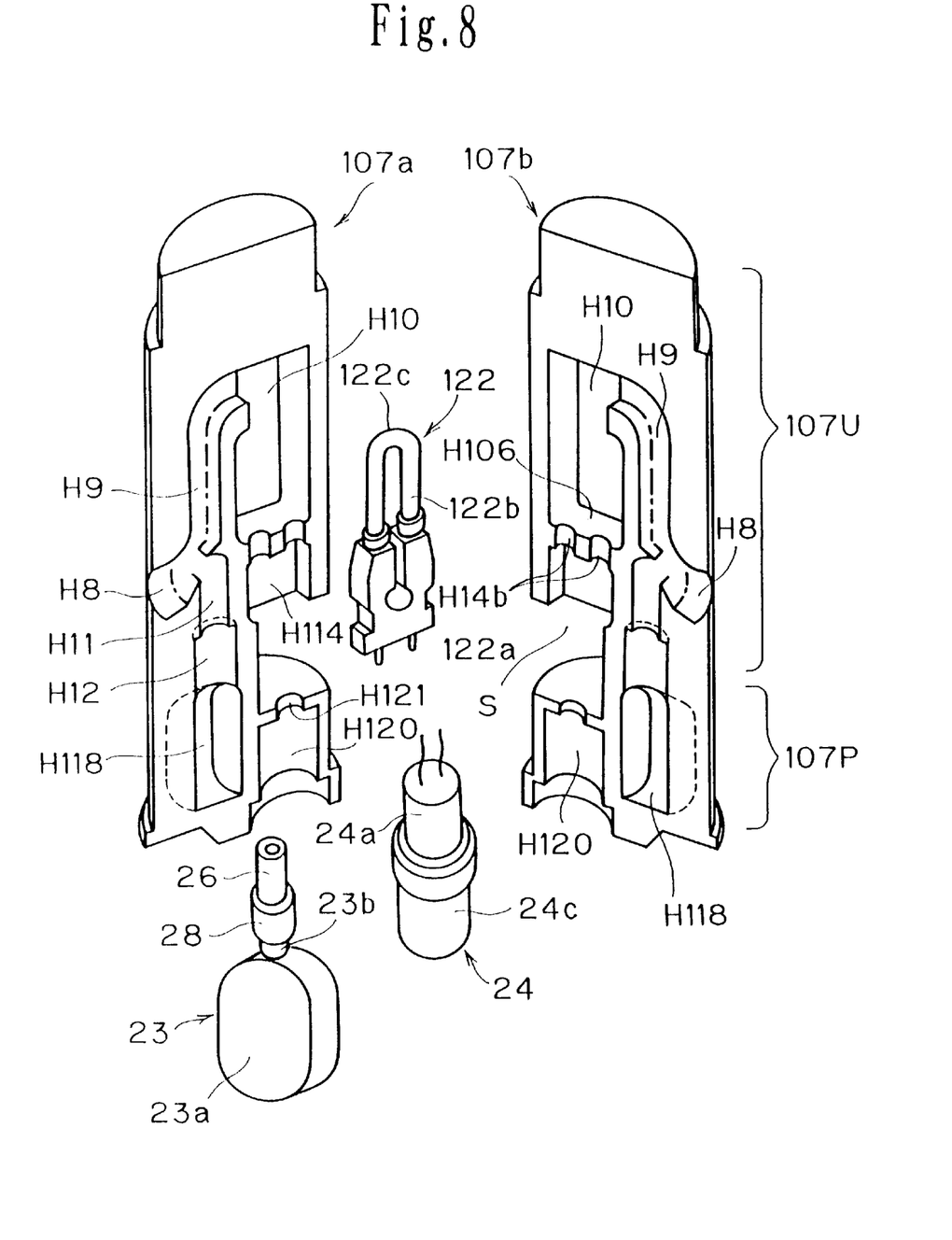
FIG. 8 is a disassembled perspective view showing an inner structure of the probe main body adopted in the other embodiment of the invention shown by FIG. 7.

FIGS. 7 and 8 show other embodiment of the invention. Although in the first embodiment described previously in reference to FIGS. 1 through 6, the article inserted to the probe main body comprises two kinds of molded articles of the plug 6 and the unit body 7, the second embodiment shown by FIGS. 7 and 8 provides an extended unit body 107 in which such two kinds of molded articles are integrated into one piece.

The extended unit body 107 is molded in a collapsible block by a fire resistant material comprising inorganic particles of foundry sand similar to the first embodiment, is integrally provided with a plug shell portion 107P facing the front end of the probe main body 1 and a unit shell portion 107U extended therefrom and comprises divided blocks 107a and 107b which are halved along the center axis line. Accordingly, by opposing and overlapping the pair of divided blocks 107a and 107b in a symmetrical shape, they are integrated substantially in a circular column shape as a whole and are internally mounted to the cylindrical body 2 of the probe main body 1.

The unit shell portion 107U is formed with the introductory path 8 opened to face the flow inlet 3 of the cylindrical body 2, the communicating path 9 extended upwardly from the introductory path 8 and the temperature measuring chamber 10 extended downwardly by being turned or folded back from the communicating path 9 and the introductory path 8 and the temperature measuring chamber 10 are arranged to allocate substantially in left and in right in respect of the center axis line of the extended unit body 107. Further, the guide path 11 extended downwardly from the introductory path 8 is formed and the holding path 12 which is extended from the guide path 11 and the inner diameter of which is expanded, is formed. According to the introductory path 8, while the lower face of the opening portion 8a facing the flow inlet 3 is formed low, a vicinity of the terminal end of the introductory path 8 is formed high by which the raised portion 8b is formed and the guide path 11 is opened at the top portion of the raised portion 8b. The communicating path 9 is provided with the linear path 9a substantially in parallel with the central axis line of the unit shell portion 107U and the inclined path 9b inclined to be bent from the linear path and extended toward the opening portion 8a of the introductory path 8 and the cover portion 8c is formed above the guide path 11. These points are the same as in the structure of the first embodiment.

However, as shown by FIGS. 7 and 8, the unit shell portion 107U is formed with a holding chamber 114 for holding a temperature sensor 122 on the lower side of the temperature measuring chamber 10 and is provided with communication holes 14b for inserting a temperature measuring pipe of the temperature sensor 122 at a partition wall 10b for partitioning the temperature measuring chamber 10 from the holding chamber 114.

The plug shell portion 107P is formed with a containing chamber 118 communicating with the holding path 12 extended from the guide path 11 and a receiving chamber 120 formed in parallel with the containing chamber 118 in a lateral arrangement and opened downwardly.

The extended unit body 107 is formed with a wire connecting space portion S disposed between the holding chamber 114 of the unit shell port ion 107U and the receiving chamber 120 of the plug shell portion 107P and opened in a side direction and a hole 121 communicating with the wire connecting space portion S is opened at the bottom wall of the receiving chamber 120.

FIG. 8 shows a state of disassembling the divided blocks 107a and 107b which are halved in a symmetrical shape and respective halves of the introductory path 8 mentioned above, the communicating path 9 and the guide path 11 which are branched from the introductory path, the temperature measuring chamber 10, the holding chamber 114, the containing chamber 118 and the receiving chamber 120 are shown. Therefore, constituent portions showing only halves thereof are designated by attaching notations adding H to notations designating respective structural constitutions mentioned above.

The extended unit body 107 is integrated with the temperature sensor 122, the sampling vessel 23 and the outside temperature measuring means 24 to thereby form the probe main body 1 according to the molten metal probe of the invention.

The temperature sensor 122 is similar to that described in U.S. Pat. No. 5,741,072 having a constitution in which a temperature measuring pipe 122b in a U-like shape is extended from a holder portion 122a, a thermocouple is provided at inside of the temperature measuring pipe 122b and a temperature sensing portion 122c is constituted by the front end portion of the temperature measuring pipe 122b. In this case, in a state in which the temperature sensing portion 122c is inserted to a predetermined position of the temperature measuring chamber 10, the temperature measuring pipe 122b is inserted into and held by the through holes 14b and a holder portion 122a is held by the holding chamber 114.

Further, pins led out from the holder portion 122a are connected to a connector (not illustrated) in the wire connecting space portion S.

According to the sampling vessel 23, the vessel main body 23a made of metal for constituting the sampling chamber 25 is contained in and held by the containing chamber 118 of the plug shell portion 107P, the collar 28 installed at the inlet portion 23b of the vessel main body 23a is fitted to the holding path 12 and the guide pipe 26 extended from the inlet portion 23b is adaptably fitted to the guide path 11. In such a state, the front end of the guide pipe 26 is disposed in flush with the top face of the raised portion 8b.

According to the outside temperature measuring means 24, the holder portion 24a is inserted into and fixed by the receiving chamber 120 of the plug shell portion 107P and the temperature measuring pipe 24b covered by the cap 24c made of metal is projected downwardly from the plug shell portion 107P. Lead wires led out from the holder portion 24a are led to the wire connecting space portion S via holes 121 and are connected there to a connector (not illustrated).

Further, it is preferable to charge a deoxidizer such as an aluminum piece to the communicating path 9, the sampling path 27 and the sampling chamber 25.

(Third Embodiment)

Figure 9:
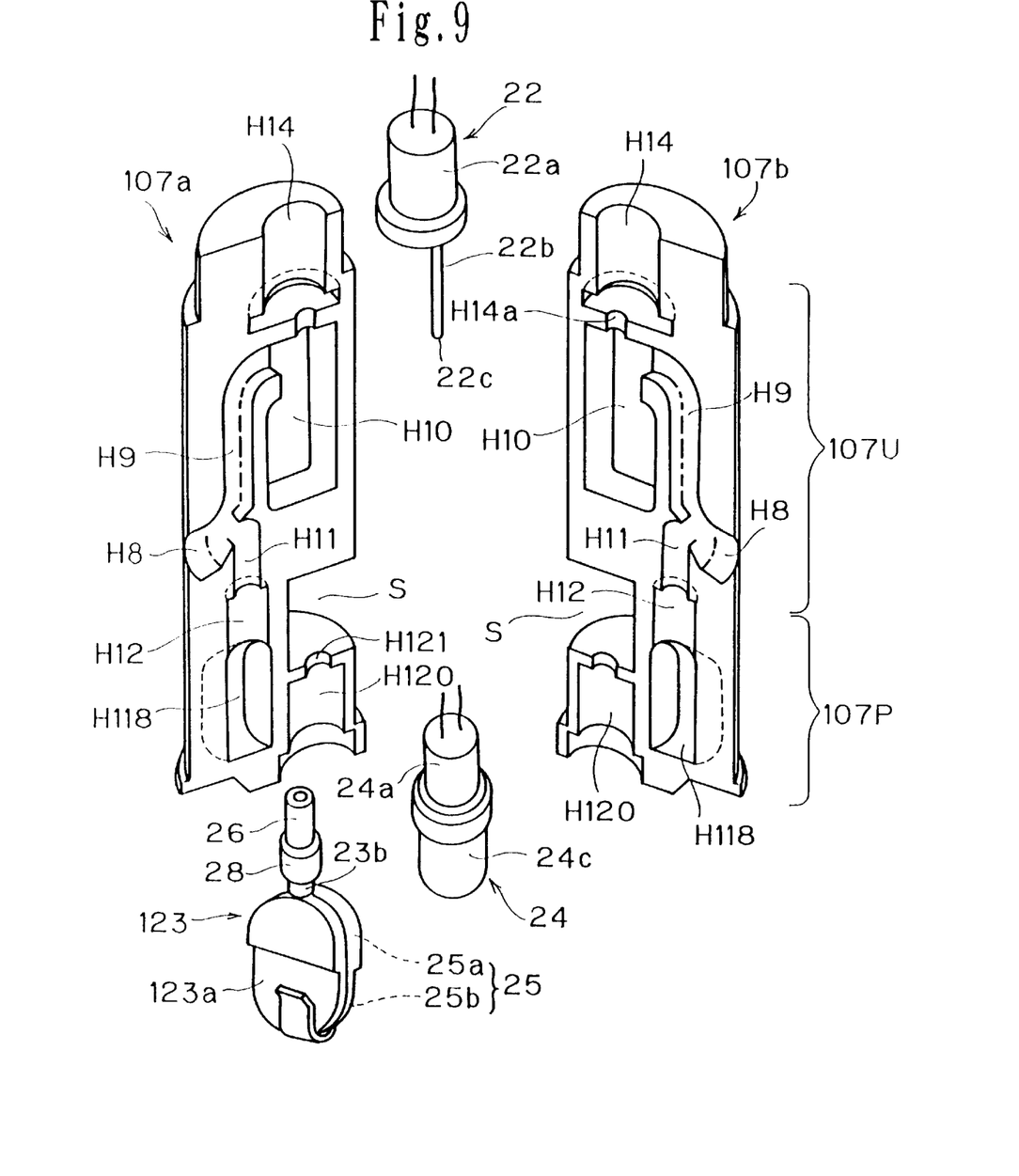
FIG. 9 is a disassembled perspective view showing an inner structure of a probe main body according to still other embodiment of the molten metal probe of the invention.

FIG. 9 shows a third embodiment of the invention and similar to the second embodiment shown by FIGS. 7 and 8, there is provided the extended unit body 107 integrally installed with the plug shell portion 107P and the unit shell portion 107U. The extended unit body 107 is integrated substantially in a circular column shape as a whole by opposing and overlapping the pair of divided blocks 107a and 107b in a symmetrical shape which are divided in two along the center axis line and is internally mounted to the cylindrical body of the probe main body similar to the second embodiment. Further, FIG. 9 shows a state where the divided blocks 107a and 107b are disassembled and notations designating respective structural constitutions are respectively attached with H.

According to the third embodiment, in the unit shell portion 107U, the holding chamber 14 is formed outside of and above the temperature measuring chamber 10, the holder portion 22a of the temperature sensor 22 is held by the holding chamber 14 and the temperature measuring pipe 22b of the temperature sensor 22 is inserted through the through hole 14a by which the temperature sensing portion 22c is made to face a predetermined position of the temperature measuring chamber 10 and this point is similar to that in the first embodiment shown by FIG. 3.

Although similar to the first embodiment and the second embodiment, according to a sampling vessel 123, the collar 28 is outwardly mounted to the inlet portion 23b of a vessel main body 123a made of metal and the guide pipe 26 is extended from the inlet portion 23b, according to the third embodiment, as shown by FIG. 9, in the flat sampling chamber 25 formed by the vessel main body 123a, a thick sampling chamber 25a is formed in the upper portion and a thin sampling chamber 25b is formed in the lower portion.

The invention can be modified variously based on the spirit of invention described in the scope of claims and it is intended to understand that the arrangement relationship between the temperature sensor and the holding chamber and the shape and the kind of the sampling vessel are not limited to those in the illustrated embodiments.

(Advantage of the Invention)

According to the embodiment, runners branched upwardly and downwardly from the introductory path 8 opened to face the flow inlet 3 are provided, the sampling path 27 constituted by the runner directed downwardly is communicated with the sampling chamber 25 and the communicating path 9 constituted by the runner extended upwardly is communicated with the upper portion of the temperature measuring chamber 10 and accordingly, storing and solidifying molten metal for providing solidification temperature data and storing and solidifying molten metal for providing a solidified sample for analysis such as instrumental analysis by the molten metal which flows in from the same position, can be carried out simultaneously by the molten metal under the same condition. Further, by respectively forming the sampling path 27 and the communicating path 9 in predetermined lengths, heat of the flowed-in molten metal can pertinently be taken out and further, the molten metal is preferably deoxidized in the flow-in procedure and accordingly, the optimum solidification temperature data can be provided and the optimum solidified sample can be provided.

Further, in this way, the introductory path 8 communicating with the temperature measuring chamber 10 and the sampling path 27 communicating with the sampling chamber 25 are branched upwardly and downwardly from the introductory path 8 and therefore, the probe main body 1 can be constituted compactly as a whole. Further, as a result, the principal inner structure of the probe main body 1 can be constituted by the unit body 7 and the plug 6 which are molded in blocks by a fire resistant material and the assembling operation is facilitated and mass production formation and low cost formation thereof can be realized.

Further, the communicating path 9 and the sampling path 27 which are branched upwardly and downwardly from the introductory path 8 are arranged not to be opposed to each other but to shift from each other in respect of the branch point, the communicating path 9 is directed to the opening 8a of the introductory path 8 and the sampling path 27 is opened at the top portion of the raised portion 8b and accordingly, when the temperature measuring chamber 10 and the sampling chamber 25 are filled with molten metal and thereafter, the probe main body 1 is pulled up, the molten metal flowing down from the communicating path 9 is not flowed to the sampling path 27 and is pertinently discharged from the introductory path 8 to the flow inlet 3. Therefore, the solidified sample 29 sampled by the sampling chamber 25 is not integrally connected to the unnecessary solidified metal 30 which remains in the temperature measuring chamber 10 or other unnecessary solidified metal, the sampling vessel 23 including the solidified sample 29 can easily be taken out from the probe main body 1 and can be preferably carried for analysis such as instrumental analysis.

Further, according to the invention, the plug 6 and the unit body 7 are molded in blocks by a collapsible fire resistant material, the upper portion of the sampling vessel 23 is loosely fitted to the free space 13 formed by enlarging the lower portion of the guide path 11 provided in the unit body 7 and in the meantime, the lower portion of the sampling vessel 23 is fittedly held by the holding recess 18 formed in the plug 6 and accordingly, in a state in which the probe main body 1 is dipped into molten metal, the sampling vessel 23 can preferably be maintained and in the meantime, after elapse of a predetermined time period, the plug 6 is made fragile and is gradually collapsed from the surface by which the sampling vessel 23 is partially exposed. Therefore, when the probe main body 1 is pulled up and is dropped onto a floor face, the sampling vessel 23 is spontaneously detached therefrom by impact or can be drawn easily by a jig and therefore, sample carrying operation by a carrying apparatus such as a pneumatic tube can be carried out swiftly and easily at the site of the operation.

Further, according to the block-molded article, when it is provided as the extended unit body 107 integrally installed with the plug shell portion 107a and the unit shell portion 107b, owing to a reduction in a number of parts, the integral body contributes to low cost and facilitated formation of assembling operation.

What is claimed is:

1. A molten metal probe which is dipped in molten metal and is thereafter pulled up therefrom comprising a probe main body (1), a flow inlet (3) provided at a side portion of said probe main body for flowing in the molten metal, a temperature measuring chamber (10) and a sampling chamber (25) separately provided in said probe main body for solidifying the molten metal flowed therein respectively, and a temperature sensor (22) arranged in said temperature measuring chamber (10); wherein runners branching upwardly and downwardly from an introductory path (8) opened to face the flow inlet (3) are provided, a sampling path (27) constituted by the downward runner is communicated with the sampling chamber (25) and a communicating path (9) constituted by the runner extended upwardly is communicated with an upper portion of the temperature measuring chamber (10).

2. A molten metal probe according to claim 1 wherein a deoxidizer is charged to at least respectives of the sampling path (27) and the communicating path (9).

3. A molten metal probe according to claim 1 wherein the sampling path (27) directed downwardly is communicated with a vicinity of a terminal end of the introductory path (8), and the communicating path (9) directed upwardly is communicated with a vicinity of an opening of the introductory path (8).

4. A molten metal probe according to claim 1 wherein a center axis line (C2) of the sampling path (27) directed downwardly and a center axis line (C3) of the communicating path (9) directed upwardly are shifted from each other, and a distance (L2) from a center axis line (C1) of the probe main body (1) to the center axis line (C2) and a distance (L3) from the center axis line (C1) to the center axis line (C3) are formed under a relationship of L2<L3.

5. A molten metal probe according to claim 1 wherein the communicating path (9) directed upwardly comprises a linear path (9a) substantially in parallel with the center axis line (C1) of the probe main body and an inclined path (9b) extended toward a vicinity of an opening of the introductory path (8) by being bent from said linear path.

6. A molten metal probe according to claim 1 wherein the introductory path (8) receives a raised portion (8b) projected upward from a lower face of the opening wall portion facing the flow inlet (3) and the sampling path (27) directed downwardly is opened at a top portion of the raised portion.

7. A molten metal probe according to claim 1 wherein;

a unit body (7) molded in a block by a collapsible fire resistant material is internally mounted to the probe main body (1);

the unit body (7) is formed with the introductory path (8) opened in a side direction, the communicating path (9) extended upwardly from the introductory path, the temperature measuring chamber (10) extended downwardly by being turned back from the communicating path, a holding chamber (14) at outside of the temperature measuring chamber for holding a temperature sensor (22) having a temperature sensing portion (22c) inserted into the temperature measuring chamber and a guide path (11) extended downwardly from the introductory path (8); and a sampling vessel (23) constituting the sampling chamber (25) provides a vessel main body (23a) of a metal with a guide pipe (26) extended therefrom and inserted into the guide path (11) to form the sampling path (27) extending downwardly from the introductory path.

8. A molten metal probe according to claim 7 wherein the unit body (7) comprises divided blocks (7a, 7b) divided in two pieces along a central axis line of the probe main body (1).

9. A molten metal probe which is dipped in molten metal and is thereafter pulled up therefrom comprising a probe main body (1), a flow inlet (3) provided at a side portion of said probe main body for flowing in the molten metal, a temperature measuring chamber (10) and a sampling chamber (25) separately provided in said probe main body for solidifying the molten metal flowed therein respectively, and a temperature sensor (22) arranged in said temperature measuring chamber (10); further comprising:

a plug (6) internally mounted to a front end portion of the probe main body and a unit body (7) internally mounted to the probe main body in a state in which the unit body (7) is connected to the plug;

wherein the plug (6) and the unit body (7) are separately formed and are molded in blocks respectively by a collapsible fire resistant material;

the unit body (7) includes an introductory path (8) opened to face the flow inlet (3), a communicating path (9) extended upwardly from the introductory path, the temperature measuring chamber (10) extended downwardly by being turned back from the communicating path, a guide path (11) extended downwardly from the introductory path (8) and a free space (13) formed by expanding a lower portion of the guide path and opened to a lower face of the unit body (7);

the plug (6) includes a holding recess (18) opposed to the free space (13); and a sampling vessel (23) constituting the sampling chamber (25) provides a vessel main body (23a) made of metal with a guide pipe (26) extended therefrom and inserted into the guide path (11), an upper portion of the vessel main body (23a) is loosely inserted to the free space (13) and a lower portion of the vessel main body (23a) is fitted to the holding recess (18).

10. A molten metal probe which is dipped in molten metal and is thereafter pulled up therefrom comprising a probe main body (1), a flow inlet (3) provided at a side portion of said probe main body for flowing in the molten metal, and a sampling chamber (25) provided in said probe main body for receiving and storing the flowed-in molten metal; further comprising:

a plug (6) internally mounted to a front end portion of the probe main body and a unit body (7) internally mounted to the probe main body in a state in which the unit body (7) is connected to the plug;

wherein the plug (6) and the unit body (7) are formed separately and molded in blocks respectively by a collapsible fire resistant material;

the unit body (7) includes an introductory path (8) opened to face the flow inlet (3), a guide path (11) extended downwardly from the introductory path and a free space (13) formed by expanding a lower portion of the guide path and opened to a lower face of the unit body (7);

the plug (6) includes a holding recess (18) opposed to the free space (13); and a sampling vessel (23) constituting the sampling chamber (25) provides a vessel main body (23a) made of metal with a guide pipe (26) extended therefrom and inserted into the guide path (11), an upper portion of the vessel main body (23a) is loosely inserted into the free space (13) and a lower portion of the vessel main body (23a) is fitted to the holding recess (18).

11. A molten metal probe which is dipped in molten metal and is thereafter pulled up therefrom comprising a probe main body (1), a flow inlet (3) provided at a side portion of said probe main body for flowing in the molten metal, a temperature measuring chamber (10) and a sampling chamber (25) separately provided in said probe main body for solidifying the molten metal flowed therein respectively, and a temperature sensor (22) arranged in said temperature measuring chamber (10); further comprising:

- an extended unit body (107) internally mounted to a front end portion of the probe main body (1) and molded in a block by a collapsible fire resistant material to form integrally a plug shell portion (107P) facing a front end of the probe main body and a unit shell portion (107U) extended therefrom; wherein

- the unit shell portion (107U) includes an introductory path (8) opened to face the flow inlet (3), a communicating path (9) extended upwardly from the introductory path, the temperature measuring chamber (10) extended downwardly by being turned back from the communicating path and a guide path (11) extended downwardly from the introductory path (8);

- the plug shell portion (107P) includes a containing chamber (118) communicating with the guide path (11) and a receiving chamber (120) arranged in parallel with the containing chamber in a laterally arranged state and opened downwardly;

- a sampling vessel (23) constituting the sampling chamber (25) provides a vessel main body (23a) made of metal with a guide pipe (26) extended therefrom and inserted into the guide path (11), the vessel main body (23a) is fitted to the containing chamber (118); and

- outside temperature measuring means (24) is inserted into and held by the receiving chamber (120).

12. A molten metal probe according to claim 11 wherein the unit shell portion (107U) provides a holding chamber (114) for holding a holder portion (122a) of the temperature sensor (122) at outside of the temperature measuring chamber, said temperature sensor (122) having a temperature sensing portion (122c) inserted into the temperature measuring chamber; and

- a wire connecting space (S) is formed to open at a side portion of the extended unit body (107) and communicates with a hole (121) opened at a bottom wall of the receiving chamber (120).

13. A molten metal probe according to claim 11 wherein the extended unit body (107) comprises divided blocks (107a, 107b) divided in two pieces along a central axis line of the probe main body.

* * * * *